United States Patent
Bonte et al.

(10) Patent No.: US 8,377,486 B2
(45) Date of Patent: Feb. 19, 2013

(54) COSMETIC COMPOSITION CONTAINING AN ADENIUM OBESUM EXTRACT, USE THEREOF AND METHOD FOR COSMETIC CARE INCLUDING THE USE THEREOF

(75) Inventors: Frédéric Bonte, Orléans (FR); Marc Dumas, Saint Jean le Blanc (FR); Jean-Christophe Archambault, Meung sur Loire (FR)

(73) Assignee: LVMH Recherche, Saint Jean de Braye (FR)

( * ) Notice: Subject to any disclaimer, the term of this patent is extended or adjusted under 35 U.S.C. 154(b) by 235 days.

(21) Appl. No.: 12/599,591

(22) PCT Filed: May 7, 2008

(86) PCT No.: PCT/FR2008/050811
§ 371 (c)(1),
(2), (4) Date: May 18, 2010

(87) PCT Pub. No.: WO2008/152268
PCT Pub. Date: Dec. 18, 2008

(65) Prior Publication Data
US 2010/0272662 A1   Oct. 28, 2010

(30) Foreign Application Priority Data
May 11, 2007 (FR) ..................................... 07 55042

(51) Int. Cl.
*A01N 65/00* (2009.01)
(52) U.S. Cl. .................................................... 424/725
(58) Field of Classification Search .......................... None
See application file for complete search history.

(56) References Cited

U.S. PATENT DOCUMENTS

| | | | |
|---|---|---|---|
| 5,104,326 A | 4/1992 | Smith et al. |
| 5,228,873 A | 7/1993 | Hirai |
| 5,334,049 A | 8/1994 | Kachlic et al. |
| 5,603,639 A | 2/1997 | Lai et al. |
| 5,865,645 A | 2/1999 | Embo et al. |
| 5,947,769 A | 9/1999 | Leonard et al. |
| 6,024,603 A | 2/2000 | Chen et al. |
| 6,077,115 A | 6/2000 | Yang et al. |
| 6,159,023 A | 12/2000 | Lai |
| 6,179,630 B1 | 1/2001 | Chang |
| 6,375,498 B1 | 4/2002 | Yu et al. |
| 6,386,910 B1 | 5/2002 | Yu |
| 6,986,681 B2 | 1/2006 | Tsai |
| 7,077,668 B2 | 7/2006 | Lapidot et al. |
| 7,090,540 B2 | 8/2006 | Masumoto et al. |
| 2006/0276064 A1 | 12/2006 | Takimura et al. |
| 2007/0015415 A1 | 1/2007 | Yang |
| 2007/0049072 A1 | 3/2007 | Sato |
| 2007/0066115 A1 | 3/2007 | Saito et al. |
| 2007/0082554 A1 | 4/2007 | Saito |
| 2007/0099512 A1 | 5/2007 | Sato |

FOREIGN PATENT DOCUMENTS

| | | | |
|---|---|---|---|
| DE | 3430251 | * | 2/1986 |
| FR | 2803523 A1 | | 7/2001 |
| JP | 61183208 | * | 8/1986 |
| JP | 2001-288113 A | | 10/2001 |
| JP | D1234789 S | | 4/2005 |
| WO | WO 96/11015 A | | 4/1996 |
| WO | WO 99/07338 A1 | | 2/1999 |
| WO | WO 2004075873 | * | 9/2004 |
| WO | WO 2008/152268 A3 | | 12/2008 |
| WO | WO 2008/152520 A2 | | 12/2008 |

OTHER PUBLICATIONS

Atawodi, African Journal of Biotechnology, vol. 4, (2), pp. 177-182, Feb. 2005.*
Nakamura et al., Natural Medicines, 54(3), 158-159, 2000.*
Adamu et al., "An ethnobotanical survey of Bauchi State herbal plants and their antimicrobial activity", Journal of Ethnopharmacology, May 13, 2005, 99(1), pp. 1-4, XP-004852864.
Pale et al., "Caracterisation et mesure des activites anti-radicalaires d'anthocyanes de plantes du Burkina Faso", Comtes Rendus Chimie, Oct. 2004, 7(10-11), 973-980, XP-004599894.

* cited by examiner

*Primary Examiner* — Michael Meller
(74) *Attorney, Agent, or Firm* — Woodcock Washburn LLP

(57) ABSTRACT

The invention relates to a cosmetic composition.
This cosmetic composition comprises an extract of *Adenium obesum*, and at least one cosmetically acceptable excipient.
This composition can be used to strengthen the cutaneous barrier, to reinforce the cohesion of the dermal-epidermal junction, to prevent or delay the effects of skin aging, or else to provide a protective, corrective, restructuring, hydrating or moisturizing effect.

27 Claims, 1 Drawing Sheet

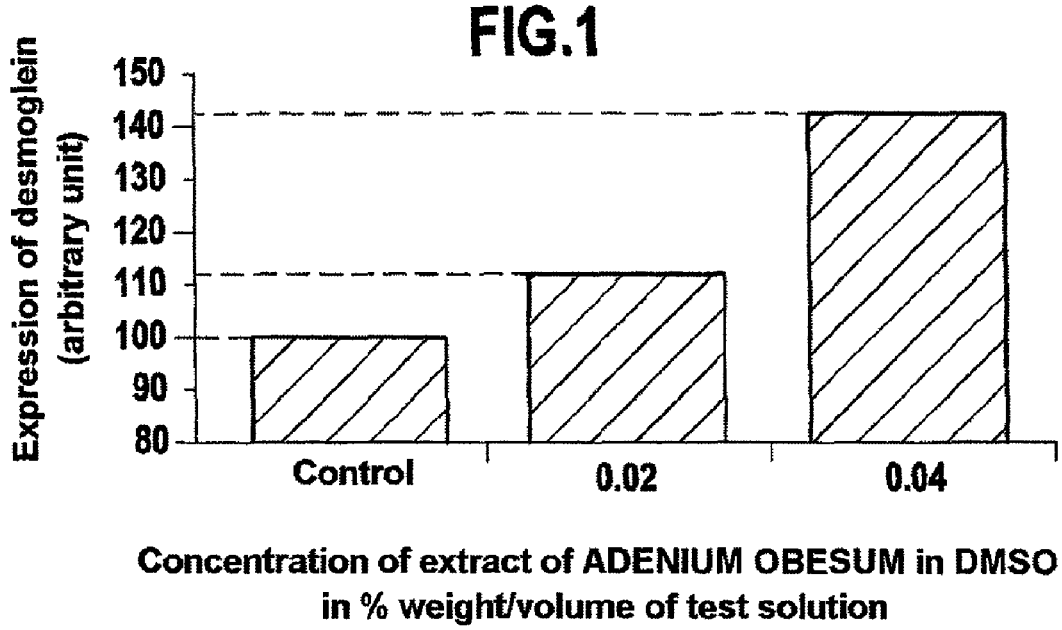
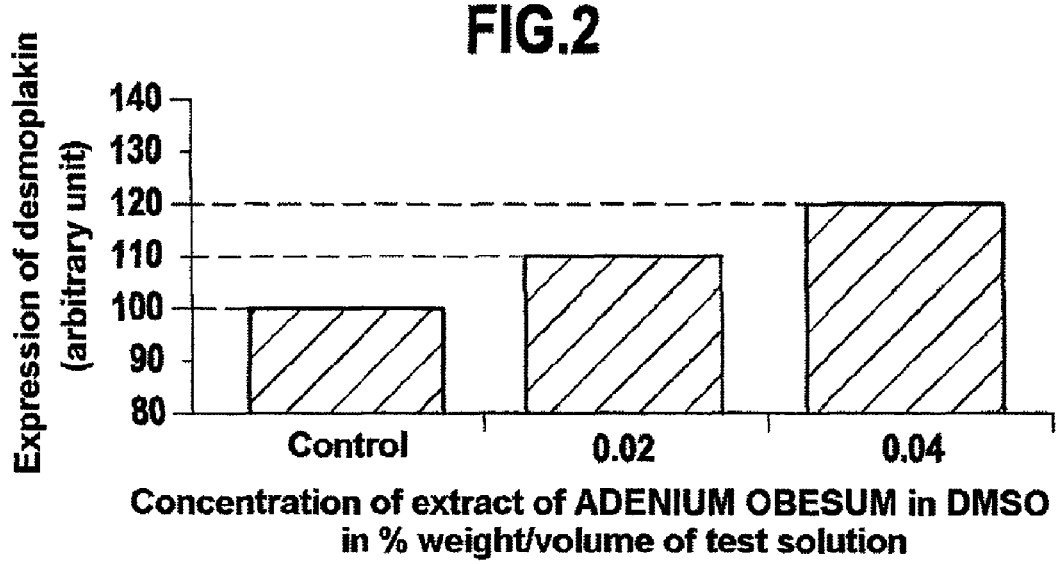

COSMETIC COMPOSITION CONTAINING AN ADENIUM OBESUM EXTRACT, USE THEREOF AND METHOD FOR COSMETIC CARE INCLUDING THE USE THEREOF

CROSS-REFERENCE TO RELATED APPLICATIONS

This application is the National Stage of International Application No. PCT/FR2008/050811, filed May 7, 2008, which claims the benefit of French Application No. 0755042 filed May 11, 2007, the disclosures of which are incorporated herein by reference in their entirety.

The present invention relates to a cosmetic composition comprising an extract of *Adenium obesum*, to a new use of an extract of this plant in the field of cosmetics, to its use especially for strengthening the cutaneous barrier and/or reinforcing the dermal-epidermal junction, and to a cosmetic care method comprising its application.

The skin is the outermost layer protecting our body.

The horny layer and the epidermis, which form the most superficial layers of the skin, must exhibit resistance to the forces and mechanical stresses which act on them, and must also exhibit resistance to evaporation of water.

The intercellular junctions of the epithelial cells, as of the epidermis, for example, may be classified into two groups, according to their ultrastructure and their function:
  adherent or anchoring junctions, also called "desmosomes", which allow the mechanical attachment of the cells to one another and reinforce the mechanical solidity of the sealing systems;
  tight junctions, also called "close junctions", which are capable of limiting the permeability of the stratified epithelium constituted by the epidermis, and which provide for water sealing between two cellular compartments.

The desmosomes are binding sites for the keratins between two cells (keratinocytes or corneocytes) and thus reinforce the adhesion of the keratinocytes with one another, of the keratinocytes with the corneocytes of the stratum, and of the corneocytes with one another.

These adherent or anchoring junctions allow groups of cells to act as solid structural units, by combining the elements of the cytoskeleton of one cell with those of another.

The filaments of keratin within the keratinocytes and corneocytes form a structural framework for their cytoplasm and provide for their resistance to the lateral and vertical forces and to the mechanical stresses that these cells undergo.

For further details, reference may be made to the document of A. H. M. Shabana et al. in Biologie infectiologie 1997, volume III, no. 1.

Desmosomes are complex structures containing two main proteins, desmoglein, a glycoprotein with a molecular weight of 160 kDa, and desmoplakin, with a molecular weight of 285 kDa, which fix the keratin filaments.

Desmosomes therefore play an essential role in these mechanisms of resistance to the forces to which the cells of the epidermis are subject, and in the prevention of evaporation of intercellular water, a phenomenon which is responsible for skin dryness and which accelerates as the skin ages.

PRIOR ART

JP 2001288113 (LION CORP) discloses a cosmetic composition comprising a substance allowing the expression of desmoglein, desmocollin or desmoplakin, the constituent proteins of the desmosomes, for the purpose of obtaining a preventive or beneficial effect on the effects of skin aging such as skin dryness or formation of wrinkles.

FR 2 803 523 (TEXINFINE SA) relates to a cosmetic composition based on algal extracts from the family of the Dictyotales, more particularly an extract of *Padina pavonica*, which causes the maturation of keratinocytes, with amplification of the synthesis of cytokeratins 1 and 10, and an increase in desmosomal proteins.

Nevertheless, Applicant that has the merit to have found, completely unexpectedly, that it is possible to stimulate the expression of the constituent proteins of the desmosomes, also called desmosomal proteins, of the cells of the human cutaneous epidermis through the use of an extract of *Adenium obesum*.

*Adenium obesum*, also called "desert-rose", is a plant belonging to the family of the Apocynaceae, with its origins in Yemen, and is cultivated as an ornamental tropical plant.

Prior studies have aimed to identify components extracted from different parts of *Adenium obesum* and their possible antioxidant or cytotoxic pharmacological activity (see Hoffman, J. Pharm. Sci. 66 (9), 1336-38 (1977) or else Pale et al., Comptes-rendus Chimie 7 (10-11), 973-80).

Moreover, document WO 96/11015 discloses a homeopathic moisturizing composition intended for absorption via the oral route.

This is because the moisturizing effect is aimed at enhancing or precipitating the passage of water and ions in the intestine. This document neither discloses nor teaches any cosmetic application or any effect on the skin. It makes no mention of any excipient.

The document abstracted as XP004852864 of Adamu et al., published in *Journal of Ethnopharmacology*, Elsevier Scientific Publishers Limited, pages 1-4, ISSN 0378-8741 is directed to the study of medicinal plants which are used locally in the treatment of various diseases. Cosmetic use is not described or even envisaged.

The document by PALE E et al., titled "Caractérisation des mesures anti-radicalaires d'anthocyanes de plantes du Burkina-Faso" ["Characterization of free-radical scavenger measurements of plant anthocyanins of Burkina Faso"], published in October 2004 in Compte-rendu Chimie, Editions Scientifiques et Médicales Elsevier, pages 973-980, ISSN 1631-0748, includes a measurement of the free-radical scavenger activity of various plants, including the flowers of *Adenium obesum*.

However, it appears that the free-radical scavenger activities of extracts of the plant *Adenium obesum*, in which the presence of a rhamnosyl is noted, are weak. Consequently, for a person skilled in the art, the free-radical scavenger activity of an extract of this plant is not significant. This document does not envisage any cosmetic uses.

Accordingly, none of the studies published to date has been interested in the possible cosmetic properties of extracts of *Adenium obesum*, and more particularly in its stimulating effect on the desmosomal proteins of the epidermis.

The Applicant has demonstrated that an extract of *Adenium obesum* stimulates the expression of proteins of the desmosomes which are present at the intercellular junctions of the cells forming the epidermis and the horny layer, and more particularly allows stimulation of the expression of desmoglein, and more particularly of desmoglein 1, or of desmoplakin, which are two of the proteins constituting the desmosomal junctions of the epidermis, which are involved in inter-keratinocyte or inter-corneocyte cohesion.

Stimulation of this kind makes it possible to increase the efficacy of these adherent junctions and thus to enhance the resistance to the stresses to which these cellular layers are subject, and limit the evaporation of intercellular water.

Thus the strengthening of the cutaneous barrier results primarily from these two physiological phenomena, which are, firstly, an enhanced resistance to the stresses to which the cells of the horny layer and the epidermis are subject, and, secondly, a greater resistance to the evaporation of intercellular water.

The Applicant has also demonstrated that the same extract of *Adenium obesum* allows stimulation of the expression of the constituent proteins of the hemidesmosomes and desmosomes at the base of the epidermis, more particularly at the dermal-epidermal junction (DEJ).

Such stimulation therefore makes it possible to reinforce the cohesion between the cellular compartments, especially between the horny layer (stratum corneum) and the living epidermis, or between the epidermis and the dermis, in other words the reinforcement of the dermal-epidermal junction.

OBJECTS OF THE INVENTION

The main object of the present invention is that of providing a new cosmetic agent or a new cosmetic composition having good activity in reinforcing the cutaneous barrier and also being capable of preventing or delaying the effects of skin aging or else of providing a substantial or enhanced moisturizing or hydrating effect.

A further object of the invention is to solve the technical problem by a solution which is particularly simple, relatively inexpensive, and can be used on the industrial and cosmetic scale.

DESCRIPTION OF THE INVENTION

The present invention accordingly provides a cosmetic composition comprising an extract of *Adenium obesum* as active agent, and at least one cosmetically acceptable excipient.

It also provides a cosmetic composition wherein said active agent helps strengthen the cutaneous barrier and/or helps reinforce the cohesion of the dermal-epidermal junction.

The cosmetic composition according to the invention comprises an effective amount of extract of *Adenium obesum* to obtain the desired effect.

The composition according to the invention thus comprises preferentially from 0.001% to 5% by weight, preferably from 0.01% to 1% by weight, of extract of *Adenium obesum*.

The extract may be obtained from the whole plant or from parts of this plant, such as, for example, the leaves, the stem, the flowers or else the roots.

Said extract may also be obtained by cultivating cells of the whole plant or of part of the plant, more particularly cells of the leaves of *Adenium obesum*, in a plant cell culture medium known to the person skilled in the art.

The extract of *Adenium obesum* is obtainable by extraction of at least part of said plant with at least one solvent selected advantageously from the group consisting of water, a C1-C4 alcohol, ethanol for example, and a glycol selected preferably from butylene glycol and propylene glycol.

The extract of *Adenium obesum* obtained by extraction may subsequently, optionally, be lyophilized or atomized to be in the form of a powder.

The powder may be used as it is in a cosmetic composition according to the invention, or may be redispersed in a solvent or a mixture of solvents.

The solvent or mixture of solvents in which the extract in the form of a powder is redispersed may be identical or different to that which was used for the extraction.

The extract of *Adenium obesum* may also be adsorbed on a support selected, for example, from the group consisting of porous or nonporous nylon powders, and micas or any lamellar mineral substance, for the purpose of its incorporation into a make-up composition such as a lipstick or a moisturizing foundation.

In this case the extract of *Adenium obesum* is preferably an aqueous extract.

It has been found, completely unexpectedly, that the extract of the invention exhibits an activity such that it helps to reinforce the cutaneous barrier, and to improve the cohesion of the dermal-epidermal junction.

The result is an improvement in the moisturizing of the skin, and an antiaging effect.

Hence it is possible to obtain attractive skin, soft skin or skin with a finer "grain".

The tests carried out by the inventors of the present invention have shown that the properties of the extract of *Adenium obesum* can also be obtained or enhanced in cosmetic compositions, with the combinations of said extract with other actives having cosmetic effects that are similar and/or complementary to the extract of *Adenium obesum*.

A first advantageous combination of the extract of *Adenium obesum* is carried out with saponins or sapogenols. These saponins or sapogenols may be obtained from various plants by extraction with a polar solvent, in particular with an alcohol or a water/alcohol mixture. Particular saponins are those extracted from soya or from the plant Medicago or from alfalfa. Particularly advantageous saponins are those obtained by extraction from the plant *Panax notoginseng*, more particularly in the form of ginsenoside-type saponin.

The Applicant's earlier document WO99/07338 has described how the saponins extracted from *Panax notoginseng*, more particularly in the form of ginsenoside-type saponin, for example, ginsenoside saponin GRb1; or GRg1; or GRd; or GR1; or GRe, and mixtures thereof, are particularly effective in stimulating the synthesis of elastin by the dermal fibroblasts; this allows them to be used as cosmetic active agents for preventing or correcting a loss of elasticity, tonicity or firmness of the skin.

The skilled person may refer to said document WO 99/07338 in order to obtain other information relating to the use of the saponins of *Panax notoginseng* and the conditions for their extraction.

With regard to the soya saponins, they are described in the Parfums Christian Dior patent application published under the U.S. Pat. No. 6,149,148 B1, which describes saponins or sapogenols which are used in cosmetics to enhance the synthesis of collagen IV. The skilled person will be able to refer to that document in order to find out the conditions for extraction of these saponins and sapogenols and the conditions for their use in cosmetics for enhancing the dermal-epidermal junction.

The aforementioned saponins or sapogenols, irrespective of their origin, more particularly in the form of plant extracts, are used via the topical route in a cosmetic composition at a concentration of between 0.001% and 5% by weight, relative to the total weight of the composition, preferably between 0.01% and 0.1% by total weight of the composition comprising them.

The combinations which are preferred for strengthening the cutaneous barrier are employed with one or more active agents selected from the group consisting of an extract of *Castanea sativa*, an extract of *Ajuga turkestanica*, mixtures of ceramides, of free fatty acids, and of sterols, ecdysterone, calcium gluconate, D-xylose, L-serine or pyrrolidonecarboxylic acid and its cosmetically acceptable salts, such as, for example, a calcium salt.

The extract of *Adenium obesum*, alone or in combination with other active agents playing a role in strengthening the cutaneous barrier, may also be combined advantageously with one or more active agents selected from the group consisting of a glycol extract of amber, succinic acid, malic acid, salicylic acid, gentisic acid, tocopherol gentisate, ectoin and/or its hydroxy derivatives, mannitol, forskolin, urea, sarcosine, trimethylglycine, creatine, glutathione, UVA and/or UVB filters, free-radical scavengers such as tocopherol, resveratrol, its monomers or oligomers, astringinin, tocotrienol or an extract of Sanguisorba officinalis, substances which are calmatives, such as tocopherol phosphate, and substances which lighten the complexion and/or which regulate pigmentary skin disorders, such as Kushenol B, arbutin, kojic acid, calcium pantothenosulfonate, an extract of liquorice, an extract of lily or a derivative of ascorbic acid or of erythorbic acid.

Further to the extract of *Adenium obesum*, said cosmetic composition comprises at least one cosmetically acceptable excipient, which may be selected from the group consisting of pigments, dyes, polymers, surfactants, rheological agents, fragrances, electrolytes, pH modifiers, antioxidants, preservatives, and mixtures thereof.

The cosmetic composition according to the invention is intended for application to all or part of the skin of the face or body.

The cosmetic composition according to the invention may be, for example, a serum, lotion, emulsion, rich cream, tinted cream or else a hydrogel, preferably a mask, or may be in the form of a stick, a lipstick for example.

The composition exhibits a particularly desired effect in preventing or delaying the effect of skin aging, and makes it possible, more particularly, to obtain a protective, corrective, restructuring, moisturizing or hydrating effect when said cosmetic composition is applied to the skin of the face or body.

The present invention also provides other subject matter, and more particularly the uses of these extracts in the field of cosmetics.

According to a second aspect, therefore, the invention further provides for the use of the extract of *Adenium obesum* as a cosmetic agent or for the preparation of a cosmetic composition intended to strengthen the cutaneous barrier, to reinforce the cohesion of the dermal-epidermal junction, to prevent or delay the effects of skin aging, more particularly the formation of wrinkles, or else to provide a protective, corrective, restructuring, hydrating or moisturizing effect.

According to a third aspect, the invention provides a cosmetic care method intended to strengthen the cutaneous barrier, to reinforce the cohesion of the dermal-epidermal junction, to prevent or delay the effects of skin aging, more particularly the formation of wrinkles, to provide a protective, corrective, restructuring, hydrating or moisturizing effect on the skin or else to combat skin weakness, characterized in that it comprises applying to at least one affected area of the skin a cosmetic composition comprising an extract of *Adenium obesum* as defined above or as described in the following description.

The embodiments of the invention, more particularly for each of the second and third aspects of the invention, result from the embodiments of the first aspect.

Other objects, features, and advantages of the invention will emerge clearly from the reading of the explicatory description which will now be given by reference to a number of examples of preparation of extracts, and to examples of cosmetic compositions which use such extracts, which are given purely by way of illustration and which therefore do not in any way limit the scope of the invention. In the examples, all of the percentages are given by weight, the temperature is in degrees Celsius, and the pressure is atmospheric pressure, unless indicated otherwise.

DESCRIPTION OF THE FIGURES

FIG. 1 shows the results obtained in the test of example 4, based on a lyophilized extract of *Adenium obesum* obtained in example 1, showing on the abscissa the concentration of the extract *Adenium obesum* in solution in DMSO, in % weight/volume (% w/v) of test solution, and on the ordinate the expression of desmoglein 1, expressed as a percentage relative to the control; the results are expressed in the form of histograms, on the one hand for a concentration at 0.02% w/v with the extract of *Adenium obesum* of the invention of example 1, and 0.04% w/v of the same extract; and FIG. 2 shows similar results, this time relating to the expression of the protein desmoplakin, for the same concentration of 0.02% and 0.04% w/v of extract of *Adenium obesum* from example 1.

EXAMPLES OF THE INVENTION

Example 1

Preparation of Extract from Leaves of *Adenium obesum*

Cells from leaves of *Adenium obesum* are cultivated by biotechnology on a conventional plant cell culture medium which is well known to the person skilled in the art, to give, after a number of weeks, undifferentiated cell aggregates, referred to as calli.

Examples of such plant cell culture media conventionally used by the person skilled in the art are described in the following works:

E. F. Georges, D. J. Puttock and J. G. Heather, (1987) Plant Culture Media, (Volume 1, Formulations and uses), Exegetics Ltd.

Dodds J. H. Roberts L. W. (1982). Experiments in Plant Tissue Culture. Cambridge Univ. Press, Cambridge. 178 pp.

Evans D. A., Sharp W. R., Ammirato P. V., Yamada Y. (1984). Handbook of Plant Cell Culture. Techniques for Propagation and Breeding. Macmillan Publ. Co., New York, 970 pp., Vols. 1 to 6.

Reinert J., Yeoman M. M. (1982). Plant Cell and Tissue Culture. A Laboratory Manual. Springer-Verlag, Berlin, Heidelberg, N.Y. 83 pp.

Sala F., Parisi B., Cella R., Cifferi O. (1980). Plant cell cultures. Elsevier/North Holland, Amsterdam.

Sharp W. R., Larsen P. O., Paddock E. F., Raghavan V. (1979). Plant Cell and tissue culture. Principles and applications. Ohio State University Press, Columbus.

Vasil I. (1985-1991). Cell Culture and Somatic Cell Genetics of Plants. Vols. 1 to 8.

Bhojwani S., Razdan I. Z. K. (1983). Plant tissue culture: theory and practice. Elsevier, Amsterdam.

Debergh P., Zimmermann (1991). Micropropagation. Technology and application. Kluwer, London.

Zyrd J. P. (1988). Cultures de cellules, tissus et organes végétaux [Plant organ, tissue and cell cultures]. Presses Polytechniques Romandes, Lausanne.

These calli are obtained by successive subculturings onto a nutrient medium containing water, sugars, mineral salts, and vitamins.

The cells are washed carefully a number of times and are lyophilized, then finely ground and screened. The lyophilizates are rich in proteins, lipids, glucose, fructose, and sucroses, in vitamins (PP, B1, B5, B6, B8, B9) and constituent elements, more particularly membrane elements.

The lyophilizate is redissolved at 10% in sterile water.

This lyophilized extract may be used as it is as a cosmetic agent or as an active principle of a cosmetic composition, and especially for carrying out the tests of example 4.

Example 2

Preparation of Extract from Aerial Parts of *Adenium obesum*

An extract of the aerial parts is carried out cold, with stirring, with distilled water and/or 10% ethanol. The plant/solvent ratio is from 1 to 10 by weight. The extract is then filtered on a 0.45 µm filter, concentrated under vacuum or lyophilized before use.

This lyophilized extract or extract under vacuum may be used as it is as a cosmetic agent or as an active principle of a cosmetic composition.

Example 3

Preparation of Extract from the Caudex of *Adenium obesum*

The caudex of *Adenium obesum* is recovered, ground, and extracted cold by maceration with stirring for 5 h, with distilled water in a ratio by weight of 1 to 20, and then filtered and lyophilized.

This lyophilized extract or extract under vacuum may be used as it is as a cosmetic agent or as an active principle of a cosmetic composition.

One variant is that of redispersion in an ad hoc medium, a glycol, for example, of said extract.

Example 4

Treatment of Human Keratinocytes and Measurement by RT-PCR (Reverse Transcription-polymerase Chain Reaction) of the Activity of the Genes Encoding the Desmosomal Proteins of the Epidermis Normal human keratinocytes are cultivated in triplicate in an SFM medium (serum-free medium; Invitrogen) containing 0.25 ng/ml of EGF (epidermal growth factor; Invitrogen) and 25 µg/ml of pituitary extract (Invitrogen) in a humidity-saturated atmosphere, at 37° C. and under 5% of $CO_2$.

The cultures are taken to confluence and then cultivated for a further 6 days (postconfluence).

They are subsequently treated for 24 h with a solution of extract of *Adenium obesum* obtained according to example 1, at 10% weight/volume (w/v) in dimethyl sulfoxide (DMSO), at final concentrations in the cultures of 0.02 and 0.04% w/v.

Control cultures which are likewise carried out in triplicate, received the same amount of DMSO solvent for the same time.

At the end of the incubation period of 24 h after extraction, the culture supernatants are removed and the carpet of cells is rinsed twice with PBS (phosphate-buffered saline, available from Invitrogen).

The cells are then lyzed in the presence of 300 µl/culture well of Trireagent™ (Sigma) and then are frozen at −80° C. until their use for extraction of the RNAs from them. The total RNAs of each cell sample are extracted in accordance with the conventional protocol supplied by Sigma.

Potentially contaminating traces of DNA are removed by treatment with the system DNA Free (Ambion).

The total mRNAs are subsequently subjected to reverse transcription in the presence of oligo(dT) primers and of the enzyme reverse transcriptase (Superscript II from Gibco) to give the corresponding total complementary DNAs (cDNAs).

A quantitative PCR reaction (polymerase chain reaction) was carried out with the Lightcycler system from Roche Molecular Systems, in accordance with the procedures recommended by the supplier.

The final reaction mixture is made up as follows:
cDNA,
specific primers (oligonucleotides) of the different targets of the study (desmoglein 1 and desmoplakin),
the reaction mixture (Roche) containing the enzyme DNA polymerase (which allows successive replicas of DNA to be formed from the initial cDNA and the specific primers), the fluorochrome SYBR Green I (aromatic organic compound of the formula $C_{32}H_{37}N_4S$, forming part of the asymmetric cyanines, which is inserted into the double-stranded DNA replicas), and magnesium chloride $MgCl_2$.

An internal cellular check on the mRNAs corresponding to a housekeeping gene (G3PDH), in other words a gene which is expressed constitutively by the cells, was carried out simultaneously with the quantification of the mRNAs of interest, as conventionally described for this method. This check makes it possible to gain separation from the variations of mRNA of interest that would not result from the action of the extract.

The results obtained for each of the proteins desmoglein-1 and desmoplakin are shown in appended FIGS. 1 and 2.

The results are expressed in arbitrary units, by which the amount expressed for each of the proteins in the control cultures (called "control" in the figures) is referred to a value of 100.

The results indicated below and shown in the figures correspond to the arithmetic mean of the expression values measured on three test cultures, this mean itself being normalized relative to the control represented by the arithmetic mean of the values obtained for the three control cultures.

Cultures Treated with an Extract of *Adenium obesum* at a Concentration of 0.02% w/v in DMSO:

|  | Test | Control |
|---|---|---|
| Desmoglein 1 | 112 | 100 |
| Desmoplakin | 113 | 100 |

Cultures Treated with an Extract of *Adenium obesum* at a Concentration of 0.04% w/v in DMSO:

|  | Test | Control |
|---|---|---|
| Desmoglein 1 | 143 | 100 |
| Desmoplakin | 120 | 100 |

Conclusion

The extract of *Adenium obesum* tested stimulates the expression both of desmoglein 1 and of desmoplakin, which are the main constituent proteins of the desmosomal junctions. Thus the extracts of *Adenium obesum* according to the invention make it possible to stimulate the expression of the mRNAs which allow the biosynthesis of desmosomal proteins.

From this, therefore, it is possible to conclude that, by virtue of the enhancement they produce of the desmosomal junctions, the extracts of *Adenium obesum* allow strengthening of the cutaneous barrier and/or reinforcement of the cohesion of the dermal-epidermal junction.

These extracts therefore constitute cosmetic agents or active principles which make it possible to prevent or delay the effects of skin aging or else to obtain a hydrating or moisturizing effect.

Example 5

Regenerating Moisturizing Serum Comprising an Extract of *Adenium obesum*

A regenerating moisturizing serum is prepared, comprising an extract of *Adenium obesum* obtained according to one of examples 1 to 3.

The formula is as follows (% expressed by dry weight relative to the weight of the composition):

| | |
|---|---|
| *Adenium obesum* extract | 0.15% |
| Ecdysterone | 0.08% |
| Hyaluronic acid | 0.4% |
| Tocopherol acetate | 0.1% |
| Glycolic acid | 0.15% |
| D-Xylose | 0.05% |
| Fragrances, preservatives | 0.2% |
| Gelled excipients and water | qs 100% |

The regenerating moisturizing serum comprising the extract of *Adenium obesum* is to be applied and allowed to penetrate before make-up is applied.

Example 6

High-protection Moisturizing Day Cream

A high-protection moisturizing day cream is prepared, comprising an extract of *Adenium obesum* obtained according to one of examples 1 to 3.

The formula is as follows (% expressed in dry weight relative to the weight of the composition):

| | |
|---|---|
| Extract of *Adenium obesum* | 0.2% |
| Extract of *Castanea sativa* | 1.0% |
| Glycol extract of *Sanguisorba officinalis* | 0.1% |
| Sodium hyaluronate | 0.4% |
| L-Serine | 0.2% |
| Ascorbyl tetraisopalmitate | 0.05% |
| Parsol MCX | 5.0% |
| Glycerol | 3.0% |
| Fragranced excipient and water | qs 100% |

The high-protection moisturizing day cream is to be applied in the mornings.

Example 7

Anti-wrinkle Restructuring Night Cream

A restructuring night cream is prepared, comprising an extract of *Adenium obesum* obtained according to one of examples 1 to 3.

The formula is as follows (% expressed in dry weight relative to the weight of the composition):

| | |
|---|---|
| Extract of *Adenium obesum* | 0.2% |
| Ceramide 3 | 0.1% |
| Hyaluronic acid | 0.4% |
| Vitamin A palmitate | 0.05% |
| Tocotrienol | 0.05% |
| Shea butter | 1.0% |
| Glycerol | 2.0% |
| Camellia oil | 2.0% |
| Madecassoside | 0.5% |
| Excipients and water | qs 100% |

The restructuring night cream is to be applied in the evenings before bed. It possesses a twin action: it moisturizes the skin deep down, by strengthening the cutaneous barrier, and it acts to counter the formation of wrinkles, by reinforcing the cohesion of the dermal-epidermal junction.

Example 8

Lightening and Moisturizing Day Care Product

A lightening and moisturizing day care product is prepared, comprising an extract of *Adenium obesum* obtained according to one of examples 1 to 3.

The formula is as follows (% expressed in dry weight relative to the weight of the composition):

| | |
|---|---|
| Extract of *Adenium obesum* | 0.2% |
| Calcium pantothenosulfonate | 0.1% |
| Extract of liquorice | 0.5% |
| Glycerol | 2.0% |
| Excipients and water | qs 100% |

Example 9

Hydrogel Mask

A hydrogel mask is prepared, comprising an extract of *Adenium obesum* obtained according to one of examples 1 to 3.

The formula is as follows (% expressed in dry weight relative to the weight of the composition):

| | |
|---|---|
| Extract of *Adenium obesum* | 0.05% |
| Calcium gluconate | 0.2% |
| Hyaluronic acid | 0.2% |
| Excipients and water | qs 100% |

Example 10

Protective Moisturizing Foundation

A protective moisturizing foundation is prepared, comprising an extract of *Adenium obesum* obtained according to one of examples 1 to 3.

The formula is as follows (% expressed in dry weight relative to the weight of the composition):

| | |
|---|---|
| Extract of *Adenium obesum* | 0.02% |
| Adsorbent nylon powder | 2.0% |
| Colored pigments | 5.0% |
| Jojoba oil | 2.0% |
| UV filters | 4.0% |
| Micronized titanium dioxide | 2.0% |
| Glycerol | 2.0% |
| Excipients | qs 100% |

The extract of *Adenium obesum* is adsorbed on the nylon powder beforehand, for use in a moisturizing foundation.

The invention claimed is:

1. A cosmetic composition comprising from 0.001% to 5%, by weight of the composition, of an extract of *Adenium obesum*,
and at least one cosmetically acceptable excipient,
wherein the cosmetic composition is in a form appropriate for application to all or part of the skin of the face or body of a human, wherein the form is a serum, a lotion, an emulsion, a rich cream, a tinted cream, a hydrogel, a mask, a stick, or a lipstick.

2. A cosmetic composition, comprising, as active agent, an extract of *Adenium obesum*; and at least one cosmetically acceptable excipient, wherein the active agent:
strengthens the cutaneous barrier in a human;
strengthens the cohesion of the dermal-epidermal junction in a human;
reduces or minimizes the effects of skin aging in a human;
reduces or minimizes the formation of wrinkles in a human;
provides a hydrating or moisturizing effect in a human;
or any combination thereof;
and wherein the cosmetic composition is in a form appropriate for application to all or part of the skin of the face or body of a human, wherein the form is a serum, a lotion, an emulsion, a rich cream, a tinted cream, a hydrogel, a mask, a stick, or a lipstick.

3. The composition of claim 2, comprising from 0.001% to 5%, by weight of the composition, of the extract of *Adenium obesum*.

4. The composition of claim 1, comprising from 0.01% to 1%, by weight of the composition, of the extract of *Adenium obesum*.

5. The composition of claim 1, wherein the extract of *Adenium obesum* is obtained from a plant part selected from the group consisting of the whole plant, the leaves, the stem, the flowers, the roots, and any mixture thereof.

6. The composition of claim 1, wherein the extract of *Adenium obesum* is obtained by cultivating cells of the whole plant in a plant cell culture medium.

7. The composition of claim 1, wherein the extract of *Adenium obesum* is obtained by cultivating cells of the leaves of *Adenium obesum* in a plant cell culture medium.

8. The composition of claim 1, wherein the extract of *Adenium obesum* is obtained by extraction with at least one solvent selected from the group consisting of water, a C1-C4 alcohol, ethanol, butylene glycol, propylene glycol, and any mixture thereof.

9. The composition of claim 1, wherein the extract of *Adenium obesunn* is subsequently lyophilized or atomized to be in the form of a powder.

10. The composition of claim 9, wherein the powder is used as such in said composition or is redispersed in a solvent or a mixture of solvents prior to incorporation into said composition.

11. The composition of claim 1, wherein the extract of *Adenium obesum* is adsorbed on a support selected from the group consisting of porous nylon powders, nonporous nylon powders, micas, and lamellar mineral substances.

12. The composition of claim 11, wherein the extract of *Adenium obesum* adsorbed on a support is an aqueous extract.

13. The composition of claim 1, further comprising an active agent comprising saponins or sapogenols.

14. The composition of claim 13, wherein said saponins or sapogenols are selected from the group consisting of soya saponins, soya sapogenols, saponins of Medicago, sapogenols of Medicago, saponins of Panax, sapogenols of Panax, notoginseng, ginsenoside saponins, ginsenoside Rb1, ginsenoside Rd; and any mixture thereof.

15. The composition of claim 1, further comprising one or more active agents selected from the group consisting of an extract of Castanea sativa, an extract of Ajuga turkestanica, a ceramide, a free fatty acid, a sterol, ecdysterone, calcium gluconate, D-xylose, L-serine, pyrrolidonecarboxylic acid, a pyrrolidonecarboxylic acid cosmetically acceptable salt, and a pyrrolidonecarboxylic acid calcium salt.

16. The composition of claim 1, further comprising one or more active agent selected from the group consisting of a glycol extract of amber, succinic acid, malic acid, salicylic acid, gentisic acid, tocopherol gentisate, ectoin , hydroxy ectoine, mannitol, forskolin, urea, sarcosine, trimethylglycine, creatine, glutathione, tocopherol, resveratrol, astringinin, tocotrienol, an extract of Sanguisorba officinalis, tocopherol phosphate, Kushenol B, arbutin, kojic acid, calcium pantothenosulfonate, an extract of liquorice, an extract of lily, ascorbic acid and erythorbic acid.

17. A method for providing cosmetic care, comprising applying to at least one area of the skin of a human in need of said cosmetic care the cosmetic composition of claim 1.

18. A method of providing cosmetic care comprising applying to at least one area of the skin of a human in need of said cosmetic care, the cosmetic composition of claim 1, wherein the cosmetic care is selected from the group consisting of:
strengthening the cutaneous barrier in a human;
strengthening the cohesion of the dermal-epidermal junction in a human;
reducing or minimizing the effects of skin aging in a human;
reducing or minimizing the formation of wrinkles in a human;
providing a hydrating or moisturizing effect in a human;
and any combination thereof.

19. The cosmetic care method of claim 17, wherein the cosmetic composition comprises from 0.01% to 1%, by weight of the composition, of the extract of *Adenium obesum*.

20. The cosmetic care method of claim 17, wherein the extract of *Adenium obesum* is obtained by cultivating cells of the leaves of *Adenium obesum* in a plant cell culture medium.

21. The cosmetic care method of claim 17, wherein the extract of *Adenium obesum* is obtained by extraction with at least one solvent selected from the group consisting of water, a C1-C4 alcohol, ethanol; butylene glycol, propylene glycol, and any mixture thereof.

22. The cosmetic care method of claim 17, wherein the extract of *Adenium obesum* is subsequently lyophilized or atomized to be in the form of a powder which is used as such or redissolved in a cosmetically acceptable solvent.

23. The cosmetic care method of claim 17, wherein the extract of *Adenium obesum* is an aqueous extract.

24. The cosmetic care method of claim 17, further comprising an active agent comprising saponins or sapogenols.

25. The cosmetic care method of claim 24, wherein said saponins or sapogenols are selected from the group consisting of soya saponins, soya sapogenols, saponins of Medicago, sapogenols of Medicago, saponins of Panax, sapogenols of Panax, notoginseng, ginsenoside saponins, ginsenoside Rb1, ginsenoside Rd; and any mixture thereof.

26. The cosmetic care method of claim 17, further comprising one or more active agents selected from the group consisting of an extract of Castanea sativa, an extract of Ajuga turkestanica, a ceramide, a free fatty acid, a sterol, ecdysterone, calcium gluconate, D-xylose, L-serine, pyrrolidonecarboxylic acid, a pyrrolidonecarboxylic acid cosmetically acceptable salt, and a pyrrolidonecarboxylic acid calcium salt.

27. The cosmetic care method of claim 17, further comprising one or more active agent selected from the group consisting of a glycol extract of amber, succinic acid, malic acid, salicylic acid, gentisic acid, tocopherol gentisate, ectoin hydroxy ectoine, mannitol, forskolin, urea, sarcosine, trimethylglycine, creatine, glutathione, tocopherol, resveratrol, astringinin, tocotrienol, an extract of Sanguisorba officinalis, tocopherol phosphate, Kushenol B, arbutin, kojic acid, calcium pantothenosulfonate, an extract of liquorice, an extract of lily, ascorbic acid, and erythorbic acid.

* * * * *

UNITED STATES PATENT AND TRADEMARK OFFICE
CERTIFICATE OF CORRECTION

PATENT NO. : 8,377,486 B2  Page 1 of 1
APPLICATION NO. : 12/599591
DATED : February 19, 2013
INVENTOR(S) : Bonte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this

First Day of September, 2015

Michelle K. Lee
*Director of the United States Patent and Trademark Office*